United States Patent
Norenberg et al.

(10) Patent No.: US 9,546,186 B2
(45) Date of Patent: *Jan. 17, 2017

(54) NON-INVASIVE DIAGNOSTIC AGENTS OF CANCER AND METHODS OF DIAGNOSING CANCER, ESPECIALLY LEUKEMIA AND LYMPHOMA

(71) Applicant: STC.UNM, Albuquerque, NM (US)

(72) Inventors: Jeffrey P. Norenberg, Albuquerque, NM (US); Richard S. Larson, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 14/451,916

(22) Filed: Aug. 5, 2014

(65) Prior Publication Data

US 2014/0341806 A1 Nov. 20, 2014

Related U.S. Application Data

(62) Division of application No. 13/854,560, filed on Apr. 1, 2013, now Pat. No. 8,834,838, which is a division of application No. 13/309,972, filed on Dec. 2, 2011, now Pat. No. 8,435,489, which is a division of application No. 11/507,846, filed on Aug. 22, 2006, now Pat. No. 8,097,237.

(60) Provisional application No. 60/710,665, filed on Aug. 23, 2005.

(51) Int. Cl.
| | |
|---|---|
| A61K 51/00 | (2006.01) |
| A61M 36/14 | (2006.01) |
| C07F 5/00 | (2006.01) |
| C07F 9/94 | (2006.01) |
| A61K 49/10 | (2006.01) |
| A61K 51/04 | (2006.01) |

(52) U.S. Cl.
CPC ........... *C07F 5/003* (2013.01); *A61K 51/0485* (2013.01); *A61K 51/0497* (2013.01); *C07F 9/94* (2013.01); *A61K 49/106* (2013.01); *A61K 51/0474* (2013.01); *A61K 51/0482* (2013.01)

(58) Field of Classification Search
CPC .................................................. A61K 51/0474
USPC ........................................................ 424/1.11
See application file for complete search history.

(56) References Cited

U.S. PATENT DOCUMENTS

| | | | |
|---|---|---|---|
| 5,635,603 A | 6/1997 | Hansen et al. | |
| 6,274,713 B1 | 8/2001 | Sieving et al. | |
| 6,881,747 B2 | 4/2005 | Larson et al. | |
| 8,097,237 B2 | 1/2012 | Norenberg et al. | |
| 8,435,489 B2 | 5/2013 | Norenberg et al. | |
| 8,834,838 B2 * | 9/2014 | Norenberg ......... | A61K 51/0497 424/1.11 |

OTHER PUBLICATIONS

Inghirami G, Wieczorek R, Zhu B.Y, et.al. Differential Expression of LFA-1 Molecules in Non-Hodgkin,s Lymphoma and Lyphoid Leukemia. Blood. 1988;72:1431-1434.
Horst E, Radaszkiewicz T, Pals ST, et.al. Expression of the leucocyte integrin LFA-1 (CD1 I a/CD 18) and its ligand ICAM-1 (CD54) in lymphoid malignancies are related to lineage derivation and stage of differentiation but not to tumor grade. Leukemia. 1991 5(10):848-53.
Bechter OE, Eisterer W, Thaler J, et.al. Expression of LFA-1 identifies different prognostic subgroups in patients with advanced follicle center lymphoma (FCL). Leukemia Research. 1999;23(5):483-8.
Larson R.S, Davis T, Bolgna C, et.al. Dissociation of I Domain and global conformational changes in LEA-1: Refinement of small molecule-I domain structure-activity relationships. Biochemistry 2005; 44:4322-4331.
Woska J.R, Shih D, Taqueti V.R, Hogg N, Kelly T.A and Kishimoto KT. A small-molecule antagonist of LFA-1 blocks a conformational change important for LEA-I function. Journal of Leukocyte Biology. 2001;70:329-334.
Gursoy R.N and Siahaan T.J. Binding and internalization of an ICAM-1 peptide by the surface receptors of T-cells. Journal of Peptide Research. 1999;53:414-421.
Randi AM and Hogg Nancy. I Domain of beta-2 Integrin Lymphocyte Function associated Antigen-1 Contains a Binding Site for Ligand Intercellular Adhesion Molecule-I. The Journal of Biological Chemistry.1994;269(17):12395-12398.
Kuriyana Y, Nakano M, Kawanishi V and Toyama K. Cytofluorometric analysis of tumor cell size and follicle formation of B-cell lymphomas. Rinsho Ketsueki. 1995 36(4):279-285.(Abstract only).
Petruzzelli L, Maduzia L and Springer T.A. Differential Requirements for LFA-1Binding to ICAM-I and LFA-1- Mediated Cell Aggregation. .Journal Immunology.1998;160:4208-4216.

(Continued)

*Primary Examiner* — Michael G Hartley
*Assistant Examiner* — Melissa Perreira
(74) *Attorney, Agent, or Firm* — Henry D. Coleman; R. Neil Sudol

(57) ABSTRACT

The present invention is directed to novel non-invasive diagnostic tools to image cancers, especially, leukemia and non-Hodgkin's lymphomas (NHL) with minimal toxicity in vivo. The present invention represents a clear advance in the art which presently relies on tissue biopsy for diagnoses of these cancers. The novel imaging probe is capable of detecting precancerous cells, as well as their metastatic spread in tissues. This represents a quantum step forward in the diagnosis and staging of NHL using non-invasively molecular imaging techniques. This novel probe will also be useful to monitor patients response to chemotherapy treatments and other interventions or therapies used in the treatment of NHL. Compounds according to the present invention may be used as diagnostic tools for a number of conditions and diseases states as well as therapeutic agents for treating such conditions and disease states.

28 Claims, 3 Drawing Sheets

(56) References Cited

OTHER PUBLICATIONS

Buckley C.D, Ferguson E.D, Littler A 1, Bossy D and Simmons DL. Role of Ligands in the activation of LFA-1. European Journal of Immunology .1997;27:957-962.

Lub M, Kooyk Y and Figdor G.C. Ins and outs of LFA-I . Immunology Today . 1995;16(10):479-483.

Kelly T A, Jeanfavre, Mcneil W D. Woska R.J and et. al. Cutting edge:: small molecule antagonist of LFA-I mediated cell adhesion. The Journal of Immunology. 1999: 5173- 5177.

Last-Barney K, Davidson W, Cardozo M, Frye LL, Grygon CA, Hopkins JL, Jeanfavre DD, Pav S, Qian C, Stevenson JM, Tong L, Zindell R, Kelly TA. Binding site elucidation of hydantoin-based antagonists of LFA-1 using multidisciplinary technologies: evidence for the allosteric inhibition of a protein—protein interaction. J Am Chem Soc. 2001;123(24):5643-5650.

Rocha M, Kruger A, Schimnacher, et.al. Dynamic Expression Changes In Vivo of Adhesion and Costimulatory Molecules Determine Load and Pattern of Lymphoma Liver Metastasis. Clinical Cancer Research. 1996;2:811-820.

Kang JH, Chung JK, Lee YJ, Shin JH, Jeong JM, Lee DS, Lee MC. Establishment of a human hepatocellular carcinoma cell line highly expressing sodium iodide symporter for radionuclide gene therapy. J Nucl Med. 2004;45 (9):1571-1576.

Norenberg JP, Krenning BJ, Konings IR, De Jong M, Garmestani K, Brechbeil MW, Atcher RW, Kusewitt DF, Gannestani K, Brechbiel MW, Kvols LK. Safety and efficacy of 213Bi-[DOTA°,Tyr']octreotide (Bi-DOTATOC) in peptide receptor radionuclide therapy (PRRT) of neuroendocrine tumors in a preclinical model. Clinical Cancer Research; Nov. 2001;v7(11), suppl. S, p. 3732S.

Delcambre C, Rernan O, Henry-Amar M, Peny AM, Macro M, Cheze S, et al. Clinical relevance of gallium-67 scintigraphy in lymphoma before and after therapy. Eur J Nucl Med 2000;27(2):176-184.

Johnston GS. Go MF, Benua RS, Larson SM, Andrews GA, Hubner KF. Gallium-67 citrate imaging in Hodgkin's disese: final report of cooperative group.J Nucl Med 1977;18(7):692-698.

Andrews GA, Hubner KF, Greenlaw RH. Ga-67 citrate imaging in malignant lymphoma: final report of cooperative group. 1978;19(9):1013-1019.

Hussain R, Christie OR, Gehski V, Barton MB, Gruenewald SM. The role of the gallium scans in primary extranodal lymphoma.1 Nucl Med 1998;39(1):95-98.

Gallamini A. Biggi A, Fruterro A, Pugno F, Cavallero G, Pregno P, et al. Revisiting the prognoistic role of gallium scintigraphy in low-grade non-Hodgkin's mphoma. Fur J Nucl Med 1997;24(12):1499-1506.

Ben-Haim S, Bar-Shalom R, Israel O, Haim N, Epelbaum R, Ben-Shachar NI, et al. Utility of gallium-67 sicntigraphy, in low-grade non-Hodgkin's lymphoma.J Clin Oncol 1996,14(6):1936-1942.

Kumar R, Maillard I, Schuster SJ, Alavi A. Utility of fluorodeoxyglucose-PET imaging in management of patients with Hodgkin's and non-Hodgkin's lymphomas. Radiol Clin N Am 2004;42:1083-1100.

Macapinlac HA. The utility of 2-deoxy-2-[18F] fluoro-d-glucose positron emission tomography and combined positron emission tomography and computed tomography in lymphoma and melanoma. Molecular Imaging and Biology 2004; 6 (4):200-207.

Pietzsch HJ, Gupta A, Reisgys M, Dreews A, Seivert S, Seifert S et al. Chemical and Biological Characterization of Technetium(I) and Rhenium(I) Tricarbonyl Complexes with Dithioether Ligands serving as Linkers for Coupling the Tc (CO)3 and Re(CO)3 Moieties to Biologically Active Molecules. Bioconjugate Chem, 2000:11(3);414-424.

\* cited by examiner

Region Analysis

Definition:      Table

| Reg | (mm) Start | (mm) Stop | (mm) Centroid | RF | Region Counts | Region CPM | % of Total | % of ROI |
|---|---|---|---|---|---|---|---|---|
| Rgn 1 | 2.6 | 38.1 | 16.4 | 0.082 | 18037.0 | 9018.5 | 86.85 | 87.59 |
| Rgn 2 | 54.6 | 98.8 | 78.6 | 0.393 | 2556.0 | 1278.0 | 12.31 | 12.41 |
| 2 Peaks | | | | | 20593.0 | 10296.5 | 99.15 | 100.00 |

NON-INVASIVE DIAGNOSTIC AGENTS OF CANCER AND METHODS OF DIAGNOSING CANCER, ESPECIALLY LEUKEMIA AND LYMPHOMA

RELATED APPLICATIONS

This application is a divisional of U.S. patent application Ser. No. 13/854,560, filed Apr. 1, 2013, now U.S. Pat. No. 8,834,838, which is a divisional of U.S. patent application Ser. No. 13/309,972, filed Dec. 2, 2011, now U.S. Pat. No. 8,435,489 issued on May 7, 2013, which is a divisional of U.S. patent application Ser. No. 11/507,846, filed Aug. 22, 2006, now U.S. Pat. No. 8,097,237 issued on Jan. 17, 2012, which claims priority from U.S. provisional application Ser. No. 60/710,665, filed Aug. 23, 2005, all of said applications is being incorporated by reference in their entirety herein.

FIELD OF THE INVENTION

The present invention is directed to novel non-invasive diagnostic tools to image cancers, especially, leukemia and non-Hodgkin's lymphomas (NHL) with minimal toxicity in vivo. The present invention represents a clear advance in the art which presently relies on tissue biopsy for diagnoses of these cancers. The novel imaging probe is capable of detecting precancerous cells, as well as their metastatic spread in tissues. This represents a quantum step forward in the diagnosis and staging of NHL using non-invasively molecular imaging techniques. This novel probe will also be useful to monitor patients response to chemotherapy treatments and other interventions or therapies used in the treatment of NHL. Compounds according to the present invention may be used as diagnostic tools for a number of conditions and diseases states as well as therapeutic agents for treating such conditions and disease states.

BACKGROUND OF THE INVENTION

A critical need exists to develop tumor-specific non-invasive imaging agents. Currently, most imaging is based on the detection of mass lesions or general metabolic activity. Imaging agents that elucidate the pathobiology of cells in the masses are lacking. Lymphomas are characterized by the clonal malignant expansion of leukocytes and tend to grow in masses. Over-expression of leukocyte-function-associated antigen-1 receptors (LFA-1) on most lymphomas with no expression on non-hematopoetic cells make them amenable targets. An allosteric inhibitor of LFA-1 has been developed, the small molecule alkyl-amino-NorBirt. Determination of its structure activity relationship has permitted modifications allowing radiometal attachment through an alkylamino linker. We postulate that radiolabeled alkyl-amino-NorBirt will retain its binding affinity towards LFA-1 and thus can be used as a non-invasive imaging agent. Our previous work has demonstrated that the radiometal, [213]Bi, can be effectively incorporated into the alkyl-amino-NorBirt. We propose to link a radiometal with good imaging characteristics to image LFA-1 overexpression in vivo. The radiolabeled alkyl-amino-NorBirt will allow imaging of lymphoma cells trafficking in the vasculature and tissues, diagnosis and staging, as well as monitoring responses to other therapeutic interventions.

BACKGROUND AND SIGNIFICANCE

Lymphoma is a cancer of the lymphatics where the white blood cells start proliferating before they are fully mature and thus cannot function properly. These abnormal cells start collecting in the lymph nodes. The lymphoma cells can be either large or small and are usually grouped together to form small cell masses. Since leukocytes play the most vital role in immunological response by migrating to the site of injury through integrins and adhesion molecules, the chance of metastasis of lymphoma cells is very high.[1, 2, 3]

Integrins are α,β heterodimers whose activation leads to a change in structure and conformation which contribute to immune function.[4, 5] One of the major membrane bound integrins receptors is $\beta_2$ integrin leukocyte function-associated antigen-1 (LFA-1), which is expressed by the leukocytes.[4, 6, 7] The α-subunit of LFA-1, has an N-terminally inserted domain (I-domain) that plays a central role in regulating ligand binding. LFA-1 receptors are expressed normally in all of the lymphoma cells and overly expressed on many lymphomas especially T-cell and B-cell neoplasms.[9, 10, 11, 12] Also known as CD11A/CD18, LFA-1 plays a crucial role in many cellular and immunological processes (migration, antigen presentation, cytotoxicity, cell proliferation and haematopoiesis) by displaying both signaling and adhesive properties. This results in binding to the extracellular matrix as well as the receptors involved in cell-cell adhesion. This is regulated by binding to ligands such as intercellular adhesion molecules 1, 2 and 3 (ICAM-1, 2 & 3).[6, 13]

LFA-1 must be activated to the extended high affinity form in order to mediate a stable adhesion with its ligand ICAM-1.[15] The resting state affinity of LFA-1 for the ICAM-1 is very low and is estimated at $10^{-15}$-$10^{-6}$ M for mice.[16] Binding of the activated LFA-1 with the ICAM-1 through its I-domain (which retains its function as an isolated protein fragment) results in cell adhesion and migration along with intracellular signals which may cause cytotoxic action, cell proliferation or apoptosis.[6]

Development of allosteric LFA-1 inhibitors can cause inhibition of early events like the cell-cell as well as cell-extra cellular matrix adhesion and will prevent metastasis of lymphoma cells.[5, 7, 17]

Recently small molecules have been developed that bind to the I-domain of the α-subunit of LFA-1 receptors and stabilize it to the low affinity state. Structure activity studies of one of such molecule, BIRT-377, suggest that it binds to LFA-1 solely through nonionic interaction.[J Am Chem Soc 123, 5643-5650] Two hydrophobic pockets of the I-domain and the aromatic rings of Birt-377 interact with each other in an edge-to-face aromatic/aromatic orientation. This binding presumably prevents displacement of the overall conformational changes of the whole protein stabilizing it in the bent, low affinity state. Many derivatives of BIRT-377 have been developed. One of them is alkylamino-NorBirt. Studies have demonstrated that this derivative retains its affinity as the original DOTA-alkylamino-NorBirt. Even in the presence of divalent cations like $Mn^{++}$ (which results in activation and small conformational changes in the I-domain), BIRT-377 and its derivative (the alkylamino-NorBirt) inhibit the ligand binding by stabilizing LFA-1 in the bent, low affinity state.[5] Thus, it prevents the ICAM-1 adhesion on LFA-1 and thereby prevents the leukocytes from migration (metastasis).[20] It also inhibits the intercellular signals (outside-in signaling) and hence affects the functional activity of cell.

Structure activity work with BIRT-377 had suggested that the hydantoin methyl group when bound to LFA-1 was oriented away from the binding site, suggesting that changes at this site would not interfere with BIRT-377 binding. The modification of Birt-377 allows a linker 1,4,7,10-tetraaza-cyclododecane-1,4,7,10-tetraacetic acid (DOTA) to be attached to the alkylamino chain resulting in DOTA-alkylamino-NorBirt. A radiometal then can be incorporated in the DOTA linker for non-invasive imaging.

There are several characteristics of Lymphoma cells and the LFA-1 receptors, which make them amenable for non-invasive imaging. They are:
The lymphoma cells grow in masses
All types of lymphoma express LFA-1 receptors
In many cases and types, the LFA-1 receptors are over expressed
Non-Haematopoetic cells do not express LFA-1 receptors
Currently very crude techniques are available for non-invasive imaging of lymphomas.

Thus the radiolabeled DOTA-alkylamino-NorBirt can potentially be used, as a non-invasive imaging tool for lymphomas.

The need for non-invasive imaging in lymphoma is very important. The current methods of staging and detecting the residual disease are very crude. Since the research is still in its early stages, we do not expect to achieve immediate diagnostic capabilities. However, detecting the residual disease after therapy and increasing the sensitivity of staging the disease can be accomplished. The advantage of this non-invasive imaging is the sensitivity with which the radiopharmaceutical can detect the disease and its spread in the body.

BRIEF DESCRIPTION OF THE INVENTION

Figure 1:
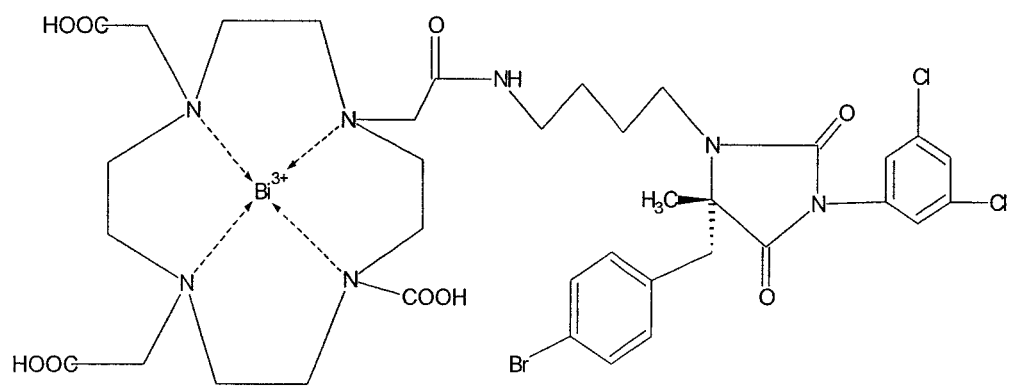
FIG. 1 shows the chemical structure of $^{213}$Bi-DOTA-alkylamino-NorBirt: 14-[5-(4-Bromo-benzyl)-3-(3,5-dichloro-phenyl)-5-methyl-2,4-dioxo-imidazolidin-1-yl]-butyl-ammonium-DOTA-$^{213}$Bi.

In the present invention, an agent for imaging cancers, in particular leukemia and lymphomas is disclosed. Compounds of the present invention have the chemical formula I:

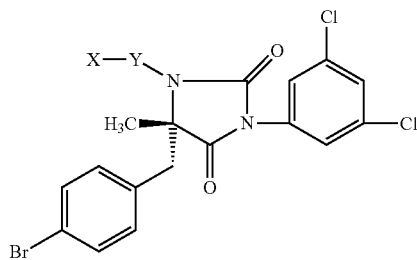

Where Y is a chemical linker which links the nitrogen to a chelate group or tricarbonyl complex X, wherein X incorporates or complexes with a radioisotope. In preferred aspects of the invention, Y is an optionally substituted $C_1$-$C_{10}$ hydrocarbyl (including an optionally substituted aryl group), preferably an optionally substituted alkyl group, for example a —$(CH_2)_n Z$— group, where n is from 1 to 6 and Z is O, NR or N—$CH_2CH_2$—O, where R is H or a $C_1$-$C_3$ alkyl (preferably H) or Z is a keto (C=O) group, a S(O)$_w$ group where w is from 0 to 4 (i.e., a sulfide, sulfoxide, sulfone, sulfonate or sulfate group), a phosphonate group or a phosphate group and X is a chelate group in which a radioisotope is incorporated or complexed. In certain preferred aspects, Y is a —$(CH_2)_n$NH— group, where n is from 1 to 6, preferably from 2 to 4, preferably 4 and X is a polyaminocarboxylic macrocycle, preferably 1,4,7,10-tetraazacyclododecane-1,4,7,10-tetraacetic acid (DOTA).

In other aspects of the invention, Y is a linker comprising a $C_1$-$C_{10}$, preferably a $C_3$-$C_8$ substituted hydrocarbyl group (which is bonded to the nitrogen of the dioxoimidazolyl group through a keto group) containing two amino groups or two sulfur groups which are linked with the tricarbonyl compound X which incorporates or complexes to the radioisotope. In certain aspects, the preferred linker contains a dithiahexyl group or a diaminohexyl or diaminobutyl group. In another aspect the linker may be derived from lysine (linked to the dioxoimidazolinyl group through the carboxylic acid moiety of lysine). Chemical linkage of the linker to the dioxoimidazolinyl group may be through a carbonyl group, alkylene group or other group capable of being linked to the nitrogen of the dioxoimidazolinyl group.

Preferred compounds according to the present invention are represented by the chemical structure:

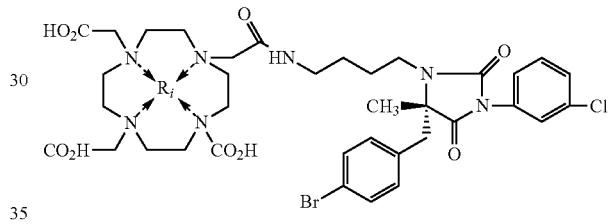

Where Rn is a radioisotope as otherwise described hereinbelow, more preferably $^{213}$Bi, $^{177}$Lu, $^{201}$Tl or $^{111}$In.

Radioisotopes are selected based on the physical half life, the decay mode (alpha, beta, auger, gamma, X-ray) and the energy of the radioisotope. Exemplary radioisotopes for use in the present invention include, for example, $^{90}$Y, $^{111}$In, $^{177}$Lu, $^{225}$Ac, $^{209}$Bi, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{99m}$Tc. In certain aspects of the present invention, preferred radioisotopes include, for example, $^{213}$Bi, $^{177}$Lu, $^{111}$In, more preferably, $^{177}$Lu and $^{111}$In, among others.

In addition to the above radioisotopes, there is also potential for the compounds to be analyzed using positron emission tomography or PET imaging when labeled with a positron emitting radioisotopes such as: $^{68}$Ga, $^{64}$Cu, $^{48}$V, $^{71}$As, $^{72}$As, $^{76}$Br, or other polyvalent, cationic radiometals that decay by positron emission.

Chelates for inclusion in the present application are selected based on the metal to be incorporated and the clinical objectives. Chelates selected for use in the present invention include those listed below.
Open-Chain Polyaminocarboxylates:
edta: ethylenediaminetetraacetic acid
dtpa: diethylenetriaminepentaacetate
AZA Macrocyclics
cyclen: 1,4,7,10-tetraazacyclododecane
cyclam: 1,4,8,11-tetraazacyclotetradecane
bridged-cyclam: 1,4,8,11-tetraazabicyclo[6.6.2]hexadecane
et-cyclam: 1,4-ethano-1,4,8,11-tetraazacyclotetradecane
cylamdione: 3,9-dioxy-1,4,8,11-tetraazacyclotetradecane diamsar: 1,8-diamino-3,6,10,13,16,19-hexaazabicyclo(6,6,6)eicosane Polyaminocarboxylic Macrocycles dota: 1,4,7,10-tetraazacyclododecane-1,4,7,10-tetraacetic acid trita: 1,4,7,10-tetraazacyclotridecane-1,4,7,10-tetraacetic acid teta: triethylenetetramine bridged-cyclam-2a: 1,4,8,11-tetraazabicyclo[6.6.2]hexadecane-1,8-di(methanephosphonic acid)

do3a: 1,4,7-tris(carboxymethyl)-1,4,7,10-tetraazacyclododecane do2a: 1,4,7,10-tetraazacyclododecane-1,7-bis(acetic acid)

Polyaminophosphonate Macrocycles dotp: 1,4,7,10-tetraazacyclododecane-1,4,7,10-tetra(methanephosphonic acid)

do3p: 1,4,7,10-tetraazacyclododecane-1,4,7-tri(methanephosphonic acid)

do2p: 1,4,7,10-tetraazacyclododecane-1,7-di(methanephosphonic acid)

Methods of diagnosing or treating ICAM-1/LFA-1 mediated diseases or conditions in a patient in need thereof, are another aspect of the invention. In this method, an effective amount of one or more compounds according to the present invention are administered to a patient in need thereof to diagnose a condition or disease state or to treat the condition or disease state. Disease states or conditions which may be diagnosed or treated by the present invention include, for example, inflammatory or immune cell-mediated diseases including arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction or use with thrombolysis agents to liquidize or eliminate thrombus, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, solid organ transplant rejection, autoimmune diseases including Raynaud's syndrome, autoimmune thyroiditis, dermatitis, multiple sclerosis, arthritis, including rheumatoid arthritis and osteoarthritis, insulin-dependent diabetes mellitus, diabetes retinopathy, uveitis, inflammatory bowel disease including Crohn's disease and ulcerative colitis, and systemic lupus erythematosus, hyperproliferative diseases such as psoriasis, hyperkeratosis, ichthyosis, keratoderma, lichen planus or warts, hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; and in adjunct therapy in reducing the likelihood of retinoic acid syndrome in an acute promyelocytic leukemia (APL) patient being treated with retinoic acid, among others.

In the diagnostic method according to the present invention, a compound according to the present invention is administered to a patient, and evidence of elevated expression of LFA-1/CAM receptors in tissue of said patient through standard well-known nuclear imaging techniques, especially radiation (radionuclide) imaging, including scintigraphic imaging, in comparison to a normal standard, is indicative of a disease state or condition in the tissue of the patient. Alternatively, positron emission tomography or PET imaging may be used, especially where the radioisotope is a positron emitting radioisotope such as $^{68}$Ga, $^{64}$Cu, $^{48}$V, $^{71}$As, $^{72}$As, $^{76}$Br, or other polyvalent, cationic radiometals that decay by positron emission. The nuclear imaging techniques useful in the present diagnostic methods are well known in the art. In general, elevated levels of radiation emanating from a diagnosed tissue is evidence of elevated LFA-1/CAM receptor activity and indicative of a disease state or condition wherein these receptors are found at elevated levels.

Pharmaceutical compositions according to the present invention include an effective amount of one or more compounds according to the present invention optionally in combination with a pharmaceutically acceptable carrier, additive or excipient. Additional pharmaceutical compositions comprise an effective amount of at least one compound, in combination with an effective amount of at least one additional active agent (a "second anti-cancer agent"), optionally in combination with a pharmaceutically acceptable carrier, additive or excipient.

Another aspect of the invention relates to a method for reducing the likelihood or preventing a patient who is at risk for a disease state or condition or will succumb to one or more of the above-described disease states comprising administering to said patient an effective amount of one or more compounds according to the present invention.

Preparation of compounds according to the present invention proceeds using standard synthetic chemical techniques which are readily available in the art. Synthetic methods for obtaining compounds related to the present invention may be found in U.S. Pat. No. 6,881,747, issued Apr. 19, 2005, which is incorporated by reference herein. These methods can serve as guides for obtaining compounds according to the present invention. In general, the present compounds may be made by condensing a chelate compound to which is bound a radionuclide onto an activated moiety containing either an electrophilic group or a nucleophilic group of a linker group which is chemically linked to the amine of the dioxoimidazolidine group of the compounds according to the present invention. Alternatively, the chelate may be first reacted with one end of a difunctional chemical linker and the unreacted moiety of the linker group may thereafter be reacted with the dioxoimidazoline group. Radioisotopes may be added (chelated) to the compound at an early or later stage in the chemical synthetic method.

As discussed above, tricarbonyl complexes may be used to prepare the final diagnostic/therapeutic compound according to the present invention. Preparation of the compound can also be prepared using Technetium (I) and Rhenium (I) tricarbonyl complexes such as those listed below using methods described by H.-J. Pietzsch, A. Gupta, M. Reisgys, A. Drews, S. Seifert, S. Seifert, et. al. [Chemical and Biological Characterization of Technetium(I) and Rhenium(I) Tricarbonyl Complexes with Dithioether Ligands Serving as Linkers for Coupling the Tc(CO)$_3$ and Re(CO)$_3$ Moieties to Biologically Active Molecules, *Bioconjugate Chem.*, 11(3) 414-424, 2000].

[Bromo(3,6-dithiaoctane-S,S)tricarbonylrhenium(I)]

[Bromo(4,7-dithia-1-octyne-S,S)tricarbonylrhenium(I)]

[Bromo(1-carboxy-3,6-dithiaheptane-S,S)tricarbonylrhenium(I)] (C$_9$H$_{12}$BrO$_5$ReS$_2$)

[Bromo(1,6-dicarboxy-2,5-dithiahexane-S,S)tricarbonylrhenium(I)] ($C_9H_{10}BrO_7ReS_2$)

[1-Carboxylato-3,6-dithiaheptane-O,S,S)tricarbonylrhenium(I) ($C_9H_{11}O_5ReS_2$)

[(1-Carboxylato-6-carboxy-2,5-dithiahexane-O,S,S)tricarbonylrhenium(I)] ($C_9H_9O_7ReS_2$)

[Bromo(1,8-dihydroxy-3,6-dithiaoctane-S,S)tricarbonylrhenium(I)] ($C_9H_{14}BrO_5ReS_2$)

[(1,8-Dihydroxy-3,6-dithiaoctane-O,S,S)tricarbonykhenium (I)]nitrate ($C_9H_{14}NO_8ReS_2$)

[Chloro(3,6-dithiaoctane-S,S)tricarbonyltechnetium(I)]

[Chloro(4,7-dithia-1-octyne-S,S)tricarbonyltechnetium(I)]

[Chloro(1-carboxy-3,6-dithiaheptane-S,S)tricarbonyltechnetium(I)]

[Chloro(1,6-dicarboxy-2,5-dithiahexane-S,S)tricarbonyltechnetium(I)]

[1-Carboxylato-3,6-dithiaheptane-O,S,S)tricarbonyltechnetium(I)

[(1-Carboxylato-6-carboxy-2,5-dithiahexane-O,S,S)tricarbonyltechnetium(I)]

The tricarbonyl complexes as described above may be reacted with the dioxoimidazoinyl compound to form a chemically linked tricarbonyl complex which contains the radioisotope.

Attachment of metal radioisotopes to the compounds prepared above make the final NorBirt diagnostic/therapeutic compounds. Analogous preparations yield compounds containing other radioisotopes as otherwise disclosed herein. Note that in Choosing Linkers:

The linkers is comprised of alkyl chains of various lengths and containing various side chains depending on the hydrophobic/hydrophilic properties of the final product and the clinical needs. Linkers preferably contain O, S or NH on the distal end of the molecule in order to attach a chelate to which may be bound a radioisotope.

Chelates:

Are selected based on the metal to be incorporated and the clinical objectives.

Chelates selected is such as those listed above and include Open-Chain Polyaminocarboxylates;

AZA Macrocyclics;

Polyaminocarboxylic Macrocycles; and

Polyaminophosphonate Macrocycles.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide, but in certain instances may also refer to stereoisomers and/or optical isomers (including racemic mixtures) of disclosed compounds.

The term "optionally substituted" shall mean a substituent other than H on a molecule of a compound, the substituent being compatible with the chemistry of the present invention. Substituents include $C_1$-$C_6$ alkyl groups (preferably, $C_1$-$C_3$ alkyl groups, which may be optionally substituted with for example, one or more halogen group, especially fluorine), halogen (F, Cl, Br or I), amine groups (which may be optionally substituted with one or two $C_1$-$C_3$ alkyl groups), $O(C_1$-$C_6)$alkyl(alkoxy), $OC(O)(C_1$-$C_6)$alkyl(ester), $(O)CO(C_1$-$C_6)$alkyl(ester), $C_1$-$C_6$ amide or $C_1$-$C_6$ carboxamide (where the amine is unsubstituted, or mono- or di-$C_1$-$C_3$ alkyl substituted), among others.

The term "effective amount" is used throughout the specification to describe concentrations or amounts of compounds according to the present invention which may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where compounds are used in combination, each of the compounds is used in an effective amount, wherein an effective amount may include a synergistic amount.

The term "ICAM-1/LFA-1 mediated disease" is used throughout the specification to describe a disease which is mediated through or occurs as a consequence of the interaction of ICAM-1 with LFA-1, for example, by inhibiting the ICAM-1/LFA-1 dependent homotypic aggregation of human lymphocytes and human lymphocyte adherence to ICAM-1, or modulating immune cell activation/proliferation, for example, as competitive inhibitors of intercellular ligand/receptor binding reactions involving CAMS and leukointegrins.

The present compounds and compositions may be used to treat varied diseases and conditions such as an inflammatory or immune cell-mediated diseases including arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction or use with thrombolysis agents to liquidize or eliminate thrombus, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, solid organ transplant rejection, autoimmune diseases including Raynaud's syndrome, autoimmune thyroiditis, dermatitis, multiple sclerosis, arthritis, including rheumatoid arthritis and osteoarthritis, insulin-dependent diabetes mellitus, diabetes retinopathy, uveitis, inflammatory bowel disease including Crohn's disease and ulcerative colitis, and systemic lupus erythematosus, hyperproliferative diseases such as psoriasis, hyperkeratosis, ichthyosis, keratoderma, lichen planus or warts, hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; and in adjunct therapy in reducing the likelihood of retinoic acid syndrome in an acute promyelocytic leukemia (APL) patient being treated with retinoic acid. The compounds according to the present invention may also be used to fluidize or dissolve a thrombus in a patient, preferably in combination with a thrombolysis agent.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all cancerous disease states and embraces or encompasses the pathological process associated with cancer, in particular hematopoietic neoplasm and its metastasis. A hematopoietic neoplasm is a neoplasm of hematopoeitic cells of the blood or lymph system and includes disease states such as Hodgkin's disease, non-Hodgkin's lymphoma, leukemias, including non-acute and acute leukemias, such as acute myelogenous leukemia, acute lymphocytic leukemia, acute promyelocytic leukemia (APL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia.

The term "prophylactic" is used to describe the use of a compound described herein which either prevents or reduces the likelihood of a condition or disease state in a patient or subject.

The term "pharmaceutically acceptable" refers to a salt form of the present compounds or a carrier, additive or excipient which is not unacceptably toxic to the subject to which it is administered.

The term "standard" is used to describe a set or reference measurement made with normal or non-diseased tissue such that a comparison with a tested sample can be made to determine the existence or absence of a disease-state or condition in the tested sample (which is usually in the patient's body). In the present invention, standards may be determined by taking measurements using normal tissue and/or the absence of a condition or disease state or a measurement, among other methods, for which the diagnostic assay is used. Standards are well known in the art and are determined using well known methods available in the art. Standards may vary from application to application depending upon the diagnostic method utilized.

The term "tumor" is used to describe a malignant or benign growth or tumefacent.

The term "anti-cancer compound" or "anti-cancer agent" is used to describe any compound (including its derivatives) other than the present compounds as otherwise described herein which may be used to treat cancer. Anti-cancer agents as described hereunder are a subset of cytotoxic agents which may be used in the present invention. Exemplary anti-cancer compounds for use in the present invention include anti-metabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

The term "coadministration" or "combination therapy" is used to describe a therapy in which at least two active compounds (one of which is a compound according to the present invention) in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., antiviral agent, antihyperproliferative disease agent, agents which treat chronic inflammatory disease, among others or as otherwise described herein).

The present invention relates to a diagnostic aspect of the invention which comprises administering a compound according to the present invention to a patient or subject to determine the existence of a disease or condition where LFA-1 expression is elevated such as in cancer, especially a leukemia or lymphoma, an inflammatory disease or an infection and through measuring the radioactive decay of the isotope through any method known in the art, as discussed above, determining the presence of leukemia or lymphoma in the patient or subject. The diagnostic method according to the present invention may facilitate therapy once diagnosis of cancer or other disease states or condition is made.

In an additional aspect of the present invention, the present compounds and compositions may be used to treat diseases and conditions which are mediated through a cellular response which is undesirable and/or which should be controlled or inhibited, especially including where LFA-1 expression is elevated. Such disease states or conditions may include inflammatory or immune cell-mediated diseases including arthritis, reactive arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, autoimmune diseases including Raynaud's syndrome, autoimmune thyroiditis, dermatitis, multiple sclerosis, rheumatoid arthritis and osteoarthritis, insulin-dependent diabetes mellitus, diabetic retinopathy, uveitis, inflammatory bowel disease including Crohn's disease and ulcerative colitis, and systemic lupus erythematosus, solid organ transplant rejection, hyperproliferative diseases such as psoriasis, hyperkeratosis, ichthyosis, keratoderma, lichen planus or warts, hematopoietic neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia, stem cell leukemia and metastasis of these diseases. Compositions according to the present invention may be used in adjunct therapy in reducing the likelihood of retinoic acid syndrome in an acute promyelocytic leukemia (APL) patient being treated with retinoic acid and can also be used to fluidize or dissolve a thrombus in a patient in combination with a thrombolysis agent. In preferred aspects the various forms of leukemia and lymphoma are advantageously treated with compounds according to the present invention.

Without being limited by way of theory, it is believed that the present compounds may be used therapeutically either by virtue of the inhibitory or stimulatory activity of the compounds within the context of the therapy of the disease state or condition.

The present invention is also directed to pharmaceutical compositions comprising an effective amount of a compound according to the present invention, including the pharmaceutically acceptable acid or base addition salts of compounds of the present invention, optionally in combination with a pharmaceutically acceptable carrier, additive or excipient.

While not being limited by way of theory, it is believed that the novel molecules of the present invention inhibit or otherwise modulate the ICAM-1/LFA-1 dependent homotypic aggregation of human lymphocytes and human lymphocyte adherence to ICAM-1. While not being limited by way of theory, it is believe that these compounds have therapeutic utility in the modulation of immune cell activation/proliferation, e.g., as competitive inhibitors or stimulators (because of the introduction of radiation) of intercellular ligand/receptor binding reactions involving CAMs and Leukointegrins. Thus the activity and therapeutic activity of compounds according to the present invention is broad-based.

Regardless of the mechanism, the compounds of the present invention may be used to diagnose, identify and/or treat conditions or disease states in patients or subjects who suffer from those conditions or disease states or are at risk for those conditions or certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus), hyperproliferative diseases, hematopoietic neoplasms. The compounds of the invention may also be used in treating asthma or as an adjunct to minimize toxicity with cytokine therapy in the treatment of cancers. In general these compounds may be employed in the treatment of those diseases currently treatable through steroid therapy.

The compounds of the present invention may be used to treat hematopoietic neoplasms and their metastasis including, for example, Hodgkin's disease, non-Hodgkin's lymphoma, leukemias, including non-acute and acute leukemias, such as acute myelogenous leukemia, acute lymphocytic leukemia, acute promyelocytic leukemia (APL), acyte T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia. In addition, the present compounds may be useful in adjunct therapy in reducing the likelihood of retinoic acid syndrome in an acute promyelocytic leukemia (APL) patient being treated with retinoic acid.

Thus, another aspect of the invention is the provision of a method for the treatment or prophylaxis of the above-described conditions in a patient in need thereof through the administration of therapeutic or prophylactic effective amounts of one or more compounds of the present invention.

In accordance with the method provided by the invention, the novel compounds of formula I in effective amounts may be administered to a patient for a diagnostic, prophylactic or therapeutic purpose either alone or with other agents, including other immunosuppressive or antiinflammatory agents or other anti-cancer agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of formula I may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount used is that amount effective within the context of the administration. A suitable oral dosage for a compound of formula I would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day, whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agents such as gemcitabine and agents based upon campothecin and cis-platin, among numerous other anti-cancer compounds including tyrosine kinase inhibitors (e.g., surafenib), EGF kinase inhibitors (e.g., tarceva or erlotinib) and ABL kinase inhibitors (e.g. gleevec or imatinib), as well as Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate;

methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anticancer agents produces a synergistic (i.e., more than additive) result which is unexpected.

The present invention also relates to pharmaceutical compositions comprising a compound according to the present invention in combination with a thrombolysis agent (such as streptokinase, tissue plasminogen activator, anisoylated plasminogen streptokinase activator complex or mixtures, thereof) to fluidize or dissolve a thrombus in a patient, optionally in combination with a pharmaceutically acceptable carrier, additive or excipient.

Compositions according to the present invention permit the incorporation of the linker and the radiometal into the small molecule. Successful incorporation of radiometals has been achieved in our laboratory.

EXAMPLES

Research Design and Methods

Radiolabelling the DOTA-alkylamino-NorBirt with $^{177}$Lu and determining its specific activity, specific binding and integrity towards LFA-1 receptors utilizing in vitro receptor studies with a lymphoma cell line.

It has been previously shown that the DOTA-alkylamino-NorBirt has affinity towards the LFA-1 receptors and specifically binds to it. This property of the DOTA-alkylamino-NorBirt will help in targeting the tumors, which over express the LFA-1 receptors. A radiometal $^{177}$Lu is selected for the following reasons:

It has a gamma photon emission of sufficient energy to image (208 keV).

It has a relatively long half life (6.72 days) allowing for a longer shelf-life and observation period.

Since DOTA is used as a cheater, $^{177}$Lu, which belongs to the lanthanide group, is suitable for incorporation so as to achieve high In-Vivo stability.

DOTA is a very effective chelator and is the most advantageous for radioactive lanthanide isotopes as they have exceptionally high thermodynamic stability and kinetic inertness. The most important part of the radiolabeling process is attaining high specific activity and stability so that the maximum amount of radioactivity can be delivered with the optimal amount of drug.

The DOTA-alkylamino-NorBirt has an affinity towards the LFA-1 receptors. The extent to which the DOTA-alkylamino-NorBirt binds to its receptors is determined by the affinity constant (Kd) of the DOTA-alkylamino-NorBirt. This affinity constant along with the 50% inhibitory concentration ($IC_{50}$) is very important to establish a dose. The Kd can be established by an equilibrium-binding assay. Since a radiometal($^{177}$Lu) is incorporated into the DOTA-alkylamino-NorBirt, an equilibrium binding assay is very important to establish and justify that the molecule retains the affinity and binding to the LFA-1 receptors to the same extent as the unlabeled DOTA-alkylamino-NorBirt. Finally, competitive binding is used to validate the assay, showing that the radiolabeled DOTA-alkylamino-NorBirt has identified the LFA-1 receptor.

Radiolabeling of the DOTA-Alkylamino-NorBirt

The radiometal, $^{177}$Lu, is incorporated into DOTA, which is linked to the small molecule. A small concentration of the DOTA-alkylamino-NorBirt is incubated with $^{177}$Lu at a buffered pH. This reaction mixture is heated at a particular temperature for a particular time. The heating time and temperature are based on the energy of activation required to completely incorporate and stabilize the radiometal into the chelator. The radiolabeling of the DOTA-alkylamino-NorBirt has been achieved in our laboratory with another radiometal, and hence the time, temperature and pH have been optimized for $^{213}$Bi. The quality control (Q.C) of the product is done to determine the percent incorporation and the radiochemical purity. Instantaneous thin layer chromatography (ITLC) in conjugation with a Bioscan (AR-2000 Imaging Scanner)/gamma counter (Wallac Wizard 1480) is used to determine the percent incorporation of radiometal into the DOTA-alkylamino-NorBirt.

The High Performance Liquid Chromatography (HPLC, Thermo Separation Products) of the radiolabeled DOTA-alkylamino-NorBirt establishes the radiochemical purity.

Materials and Method:

$^{177}$Lu is used as radiometal for labeling the DOTA-alkylamino-NorBirt. The alkylamino-NorBirt is provided by Dr. Richard Larson, University of New Mexico. DOTA is obtained from the commercial sources that have provided this service in the past. A novel radiolabeling method has been developed in our laboratory. The DOTA-alkylamino-NorBirt has been successfully labeled with $^{213}$Bi (t1/2=45.5 minutes) in our laboratory. Labeling efficiencies as high as 90% have been achieved using DOTA (metal chelator) as the linker. It is possible to achieve this same labeling efficiency with $^{177}$Lu (t1/2=6.72 days).

Approximately 10 µg of the DOTA-alkylamino-NorBirt is incorporated with 'W' mCi of $^{177}$Lu in an ependorff metal free tube. The reaction tube is buffered with 3M-ammonium acetate to pH 'X'. Then the tube is heated on the hot block at 'Y'° C. for 'Z' minutes. Following incubation, 100 µl of the reaction mixture is mixed with 200 µl of 4 mM diethylenetriaminepentaacetate (DTPA). The DTPA is added to the radiolabeled product to chelate any free $^{177}$Lu. The mixture (approximately 104) is spotted at a point 1 cm from the bottom of an ITLC silica gel coated fiber sheet (Gelman Sciences, Inc. Ann Arbor, Mich.) and then developed in a chamber using 0.9% NaCl solution as the mobile phase. The solvent front is allowed to migrate on the strip until it reaches 8 cm. This procedure is repeated so that all samples is run in duplicate. The developed strip is scanned on the BioScan® to obtain the percent incorporation. Activity retained at the bottom (origin) of the strip is the radiolabeled DOTA-alkylamino-NorBirt. Activity located at the top (solvent front) is the free $^{177}$Lu (DTPA-$^{177}$Lu). For HPLC analysis of the radiolabeled DOTA-alkylamino-NorBirt, 10 ul of the DTPA mixture is injected on a C-18 analytical reversed phased chromatography column (5 µm×250 mm) and eluted with an isocratic solvent system of 100% Methanol and water in a ratio of 65:1, flow rate 1.0 mL per minute.

Data Interpretation:

For ITLC, the activity at the origin and the solvent front is determined with the Bioscan® yielding peaks for the $^{177}$Lu-DOTA-alkylamino-NorBirt and free $^{177}$Lu ($^{177}$Lu-DTPA). The area under the curve of the peaks on integration gives counts per minute (CPM). The ratio of the CPM of the labeled DOTA-alkylamino-NorBirt (origin CPM) to total CPM (origin CPM+solvent front CPM) will give the percent incorporation. The variables, W, X, Y, and Z is adjusted until a percent incorporation of ≥90% is achieved.

A single radiometric peak is expected for the radiolabeled DOTA-alkylamino-NorBirt on the HPLC using a radiometric detector. The more hydrophilic product, the free $^{177}$Lu ($^{177}$Lu-DTPA), is expected to come off immediately and the more hydrophobic radiolabeled DOTA-alkylamino-NorBirt should come off the column much later. To determine the radiochemical purity of the DOTA-alkylamino-NorBirt, the area under the curve for each of the peaks is assessed using Win-Flow software. The $^{177}$Lu-DOTA-alkylamino-NorBirt should have approximately same retention time as the unlabeled DOTA-alkylamino-NorBirt.

In Vitro Binding Studies

Approach:

The T-cell lymphoma cell line (ESBL cell line) expressing LFA-1 receptors is used to determine the affinity constant for the radiolabeled DOTA-alkylamino-NorBirt. The ESBL cells are chosen because these same cells is used to grow tumor in mice. The equilibrium-binding assay measures the affinity of the DOTA-alkylamino-NorBirt towards its receptors. The primary aim is to determine the specific binding of the DOTA-alkylamino-NorBirt towards the target receptors (saturation binding). This analysis is dependent on the assumption that the incubation has reached equilibrium. Reaching this state of equilibrium depends upon many factors including: the characteristics of the small molecule and the LFA-1 receptors, the incubation time and temperature, as well as other experimental factors. The specific binding is used to calculate the Kd. Lower the value of Kd for the DOTA-alkylamino-NorBirt; greater is the affinity for the receptors.

The competitive binding measures the binding of a single concentration of the radiolabeled DOTA-alkylamino-NorBirt in the presence of various concentrations of the unlabeled DOTA-alkylamino-NorBirt. The competitive binding is used to determine the $IC_{50}$ (the concentration of unlabeled drug that blocks half of the specific binding).

Materials and Method:

The non-specific binding is determined using cells (5 tubes with $1*10^6$ ESBL cells/ml per tube) pre-treated with a 500-fold excess of the non-labeled DOTA-alkylamino-NorBirt and allowing it to incubate for 1 hour on ice (to saturate the binding sites). After the non-labeled DOTA-alkylamino-NorBirt has saturated the binding sites, the cells is treated with varying concentrations of the radiolabeled DOTA-alkylamino-NorBirt. Total binding will next be determined using a second set of cells (5 tubes with $1*10^6$ ESBL cells/ml per tube) treated with varying concentrations (20-500 nm) of the radiolabeled DOTA-alkylamino-NorBirt (in the absence of the unlabeled drug). In order to study the high affinity state for the receptors, a third set of (5 tubes with $1*10^6$ ESBL cells in 1 ml/tube) is treated with 1 mM Mn2+ ions and incubated for 15 minutes on ice. Varying concentrations (20-500 nm) of the radiolabeled DOTA-alkylamino-NorBirt is added to the tubes containing the treated cells. All sets of treated cells is incubated for 1 hour on ice. The treated cells is centrifuged after incubation and washed with ice-cold buffer (to minimize binding disturbance). This procedure is repeated two times. Then cells will then be counted on the gamma counter. The counts from the cells without the block will give the total binding. The non-specific binding is obtained from the blocked cells. The high affinity state binding is obtained from the cells treated with manganese ions.

The difference between the total binding and the non-specific binding provides the specific binding of the radiolabeled DOTA-alkylamino-NorBirt towards the LFA-1 receptors.

Finally, competitive binding is used to validate the assay, showing that the radiolabeled DOTA-alkylamino-NorBirt has identified the LFA-1 receptor. The concentration of the radiolabeled DOTA-alkylamino-NorBirt to be used is based on the Kd obtained. The unlabeled DOTA-alkylamino-NorBirt is used at 10 concentrations and is incubated with the single concentration of the radiolabeled DOTA-alkylamino-NorBirt. The treated cells is centrifuged after incubation and the cells is washed with ice-cold buffer (to minimize binding disturbance). This procedure is repeated two times. Then cells will then be counted on the gamma counter.

Data Interpretation:

CPM versus concentration of the radiolabeled small molecule is plotted for the non-specific and total binding. The difference between the non-specific and the total binding is the specific binding. A scatchard plot is prepared of the specific binding, as the X-axis, and the ratio of the specific binding to the concentration of the free radioligand, as the Y-axis. Kd is determined using the negative reciprocal of the slope. The DOTA-alkylamino-NorBirt retains its affinity in the presence of the radiometal. If the binding is less than expected, we increase incubation so that the optimal Kd is obtained.

For the competitive binding, a graph is made with the total radioligand binding versus the log of the unlabeled DOTA-alkylamino-NorBirt. The concentration of the unlabeled drug corresponding to the $IC_{50}$ is determined using non-linear regression.

Example

To Study Trafficking of Circulating Cells in the Vasculature and Tissues by Using a Mouse Model of Non-Hodgkins Lymphoma The In Vivo study is performed in a normal mouse model injected with $1 \times 10^6$ ESBL cells study the trafficking of circulating cells in the vasculature and tissues by using a mouse model of Non-Hodgkins lymphoma. These mice image after injection with the novel $^{177}$Lu-DOTA-alkylamino-NorBirt. These mice are then imaged continuously over a 2 week period while the tumor model is circulating in the mice and growing. Imaging studies will determine whether the drug molecule reaches a specific target area(s) or remains in circulation. The results of the imaging study also determine the mean residence time of the drug in and to the organ(s) of interest as well as the accumulative absorbed dose for the target organs and the non-specific organs of the body. This is important for the dosimetry to determine potential toxicity. Thus based on the results of the In Vivo studies, the appropriate dose can be determined in order to get the maximum imaging ability and the minimal toxicity to the dose limiting organs. The advantages of performing imaging studies immediately after injection and over time is it will allow us to track the lymphoma cells.

Methods and Materials:

For the tracking of cells circulating, three DBA/2 mice is used at each of the time points selected based upon the pharmacokinetic data obtained in specific aim 1 (anticipated to be 1, 4, 24, 48 and 72 hours) and then every 24 hours for a period of two week. The animals is re-injected with the $^{177}$Lu-DOTA-alkylamino-NorBirt such that not less than 50% of the drug has been eliminated. Therefore the animals is reinjected with the radiolabeled drug whenever it is required.

Three anaesthetized DBA/2 mice will receive an injection of 1×10$^6$ ESBL cells via the tail vein. One hour after injection, three of these mice will receive approximately 100 uCi of $^{177}$Lu-DOTA-alkylamino-NorBirt via tail vein injection. The animals is imaged using a large field-of-view gamma camera to identify any areas of localization at the five time points post injection. Animals is placed supine on a Searle gamma camera with a medium energy, parallel-hole collimator. A standard prepared by diluting the injected 1:10,000 (≤1 uCi) is placed within the field of view. Images is acquired over and the data is recorded using Pinnacle imaging computer (Medasys, Ann Arbor, Mich.). Static scintigraphic images is acquired using a 64×64 matrix. Regions of interest is defined for each foci of localized radioactivity and including each organ of interest.

Data Interpretation:

The imaging data acquired with the Pinnacle imaging computer (Medasys, Ann Arbor, Mich.). will examine the foci of uptake. The soft tissue is used as the background and is compared to the injected dose. Whole body images is decay corrected, and then regions of interest is drawn over the 13 organs. A box is drawn around the whole animal in each image at the same time points to represent the counts from the total injected dose given during the study. The counts in each area of interest or organ is converted to a percentage of total body counts. The distribution percentages in a given organ for each animal is averaged, and standard errors is calculated.

Example

To Determine the Precise Localization of Tumors within Organs by Imaging Tumor-Bearing Mice with NHL Rationale:

Cellular and tissue localization of the radiolabeled small molecule allows in vivo visualization of the trafficking and localization of cancerous cells and tumors within organs. A previously developed NHL mouse model is used. The high target-to-background ratio of the novel radiolabeled small molecule allows successful imaging of the tumors in these tumor-bearing mice. A study is performed to see if better images are achieved with a higher dose of the DOTA-alkylamino-NorBirt, then a study is performed to determine the lowest treatment dose.

Methods and Materials:

Nine anaesthetized DBA/2 mice receive an injection of 1×10$^6$ ESBL cells via the tail vein. Two weeks after injection, three of these mice receive approximately 100 μCi of $^{177}$Lu-DOTA-alkylamino-NorBirt via tail vein injection. Mice are injected with three different log based doses of the DOTA-alkylamino-NorBirt based on the Kd50 (1, 10, and 100 times the Kd). The animals are imaged using a large field-of-view gamma camera to identify any areas of localization at the five time points (anticipated to be 1, 4, 24, 48 and 72 hours) post injection. Animals is placed supine on a Searle gamma camera with a medium energy, parallel-hole collimator. A standard prepared by diluting the injected 1:10,000 (≤1 uCi) is placed within the field of view. Images are acquired over and the data is recorded using Pinnacle imaging computer (Medasys, Ann Arbor, Mich.). Static scintigraphic images is acquired using a 64×64 matrix. Regions of interest are defined for each foci of localized radioactivity and including each organ of interest. Nine anaesthetized DBA/2 mice receive an injection of 1×10$^6$ ESBL cells via the tail vein. Two weeks after injection, three of these mice receive approximately 100 μCi of $^{177}$Lu-DOTA-alkylamino-NorBirt via tail vein injection. Mice are injected with three different log based doses of the DOTA-alkylamino-NorBirt based on the Kd50 (1/10, 1/100, and 1/1000 times the Kd). The animals are imaged using a large field-of-view gamma camera to identify any areas of localization at the five time points (anticipated to be 1, 4, 24, 48 and 72 hours) post injection. Animals are placed supine on a Searle gamma camera with a medium energy, parallel-hole collimator. A standard prepared by diluting the injected 1:10,000 (≤1 uCi) is placed within the field of view. Images are acquired over and the data is recorded using Pinnacle imaging computer (Medasys, Ann Arbor, Mich.). Static scintigraphic images is acquired using a 64×64 matrix. Regions of interest is defined for each foci of localized radioactivity and including each organ of interest.

Data Interpretation:

The imaging data acquired with the Pinnacle imaging computer (Medasys, Ann Arbor, Mich.). will examine the foci of uptake. The soft tissue is used as the background and is compared to the injected dose. Whole body images is decay corrected, and then regions of interest is drawn over the 13 organs and the tumor regions. A box is drawn around the whole animal in each image at the same time points to represent the counts from the total injected dose given during the study. The counts in each area of interest or organ is converted to a percentage of total body counts. The distribution percentages in a given organ for each animal is averaged, and standard errors is calculated Example Establishment of the Pharmacokinetic Profiles and to Evaluate the Safety and Toxicity of the Radiolabeled Small Molecule in Normal Mice Rationale:

Cellular and tissue localization of the radiolabeled small molecule allows in vivo visualization of the trafficking and localization of cancerous cells and tumors within organs. A previously developed NHL mouse model is in place. The high target-to-background ratio of the novel radiolabeled small molecule allows successful imaging of the tumors in these tumor-bearing mice. The In Vivo studies are performed in a normal mouse model to determine the In Vivo pharmacokinetic profile of the drug molecule being evaluated. A mouse model is used to determine if the $^{177}$Lu-DOTA-alkylamino-NorBirt is being metabolized after injection. The drug molecule maintains its integrity and behaves in same manner In Vivo as it does In Vitro in order to achieve the maximum desired effects. Thus the drug exhibits In Vivo drug stability. The pharmacokinetic study is performed to determine the mean residence time and blood clearance of the injected drug. The pharmacokinetic study uses a specific dose of the drug molecule determined from the In Vitro data, which is injected in a mouse. The safety and toxicity of the $^{177}$Lu-DOTA-alkylamino-NorBirt is studied by in normal mice. The mice is sacrificed after 6 weeks and 6 months to determine the effects the compound has on any of the mice organs as well as evaluating many toxicity parameters.

Step 1: Pharmacokinetic Study

Approach:

The $^{177}$Lu isotope selected is optimal for the pharmacokinetic analysis; the longer half-life increases the detection time for radiometric analysis. Individual urine and blood samples are collected from mice injected with the radiolabeled DOTA-alkylamino-NorBirt. Analysis of the samples are performed using high-pressured liquid chromatography (Thermo Separation Products) with a radiometric detector (IN/US gamma ram).

Methods and Materials:

The In Vivo stability of the DOTA-alkylamino-NorBirt and the pharmacokinetic data is obtained using normal DBA2/mice. The model selected is a male, DBA/2 mouse, 6 to 8 weeks in age. Mice are housed 7 to 14 days prior to use to allow them to acclimate to their new environment. Fifteen healthy mice are used. Based on the dose established using the In Vitro studies, the labeled DOTA-alkylamino-NorBirt is injected in the mice via the tail vein. Each injected is counted on a gamma counter prior to injection. The mice is placed in metabolic cages so that urine samples can be collected. 50 μl of blood is withdrawn at each time point from each mouse (1, 4, 24, 48, and 72 hours). Each sample is weighed and then counted on the gamma counter. All the samples at each time point are centrifuged at 450 g so as to separate the plasma using a microcentrifuge. 10 μl of plasma are added to 200 μl of the 4 mM DTPA solution and 10 μl of this solution is injected on the HPLC. The radiometric peaks for the plasma samples are compared with the radiometric peak obtained using the injected (the radiolabeled DOTA-alkylamino-NorBirt). The same procedure is followed for all the five time points. Also, urine samples are collected for the same time points and analyzed in the same manner as above (however the urine samples will not require centrifugation but they will require filtration to avoid harming the HPLC column.). Fifteen additional mice are injected with the free $^{177}$Lu as the control. The same assays are performed to see the differences between the radiolabeled and the free $^{177}$Lu.

Data Analysis:

The In Vivo stability is established if the radiometric peak of the standard has almost the same retention time as the injected DOTA-alkylamino-NorBirt obtained in the plasma and the urine. The retention time is determined using the Win-Flow software (used with the radiometric detector). Also the Percent Injected Activity in the blood, plasma and urine is determined by comparison to the radiometric peaks of the injected. Using Win-Nonlin software, the mean residence time and blood clearance of the drug is calculated. Therefore, the pharmacokinetics of the radiolabeled DOTA-alkylamino-NorBirt is established. One potential problem that may occur is that not enough activity is obtained in the 10-μL-plasma DTPA sample, so a larger volume, 100 μL, is used Step 2: Safety and Toxicity Approach:

A chronic (6 months) and an acute (6 weeks) toxicity study is performed on the optimal dose and the optimal amount of activity with the best treatment regime (determined in the tumor imaging study, Aim 3) in non-tumor bearing mice. The toxicity study will begin in year two or year three and will require a veterinarian pathologist(s) to assist with histopathology. Through our existing collaborations with Lovelace Respiratory Research Institute such personnel are available to us through a professional services agreement with the UNM HSC.

Methods and Materials:

Six week old non-tumor bearing DBA/2 mice is injected with the radiolabeled DOTA-alkylamino-NorBirt in the acute toxicity study. Six weeks after the last injection of the radiolabeled DOTA-alkylamino-NorBirt, a group of five mice is sacrificed. Several organs of these rats is examined histologically (kidney, liver, pancreas, pituitary, spleen, adrenal, bone marrow, bladder and testes) by the veterinary pathologist(s).

Blood samples are obtained (by cardiac puncture) at this time in order to examine the effects of the PRRT on different organs or tissues by follow up of endocrine (pituitary, adrenals, pancreas) and non-endocrine (liver, kidney, bone marrow) functions. The following measurements are done:

| Organ | Toxicity Monitoring Parameter |
| --- | --- |
| Liver Function: | LDH, Bilirubin, ALAT, ASAT, total serum protein |
| Haematology: | Hgb, Hct, RBCs, WBCs w/differential, platelets |
| Kidney Function: | Serum creatinine, creatinine clearance, total protein |
| Pancreas Function: | Glycosylated Hgb |
| Pituitary Function: | ACTH, IGF-1, LH, FSH, TSH |
| Adrenal Cortex Function: | Corticosterone |
| Gonads: | Testosterone |
| Thyroid: | Free $T_4$ |

At the correct time point, twenty-four hours before sacrifice, the mice is placed in a metabolic cage to collect 24-hour urine. The following may be determined: creatinine clearance, β-2-microglobulin, excretion of Na$^+$, K$^+$, CL$^-$. Also, for the six-week study an HPLC analysis of the urine is performed to investigate the (amount of) radioactive metabolites. At this moment hematological and endocrine functions are checked as described for the acute experiment.

Six week old non-tumor bearing DBA/2 mice is injected with the radiolabeled DOTA-alkylamino-NorBirt in the chronic toxicity study. Six months after the last injection of the radiolabeled DOTA-alkylamino-NorBirt, a group of five mice is sacrificed. In the chronic long-term experiment (6 months) creatinine clearance and hematological determinations is done at 16 weeks as well as at the six month period.

Data Analysis is performed to determine if the radiolabeled small molecule has caused damage to any of the tissues or fluids by the specimens collected. The lesions seen in any of the organs are scored to determine any toxicity or safety problems affiliated with the $^{177}$Lu-DOTA-alkylamino-NorBirt.

Figure 2:
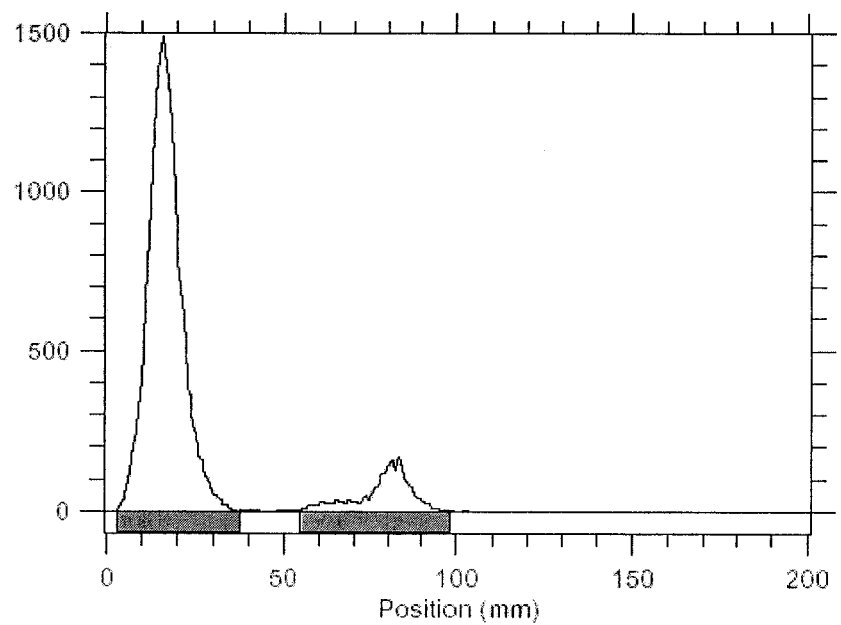
FIG. 2 shows a representative chromatogram of $^{213}$Bi-DOTA-alkylamino-NorBirt obtained on the Bioscan®.
Figure 3:
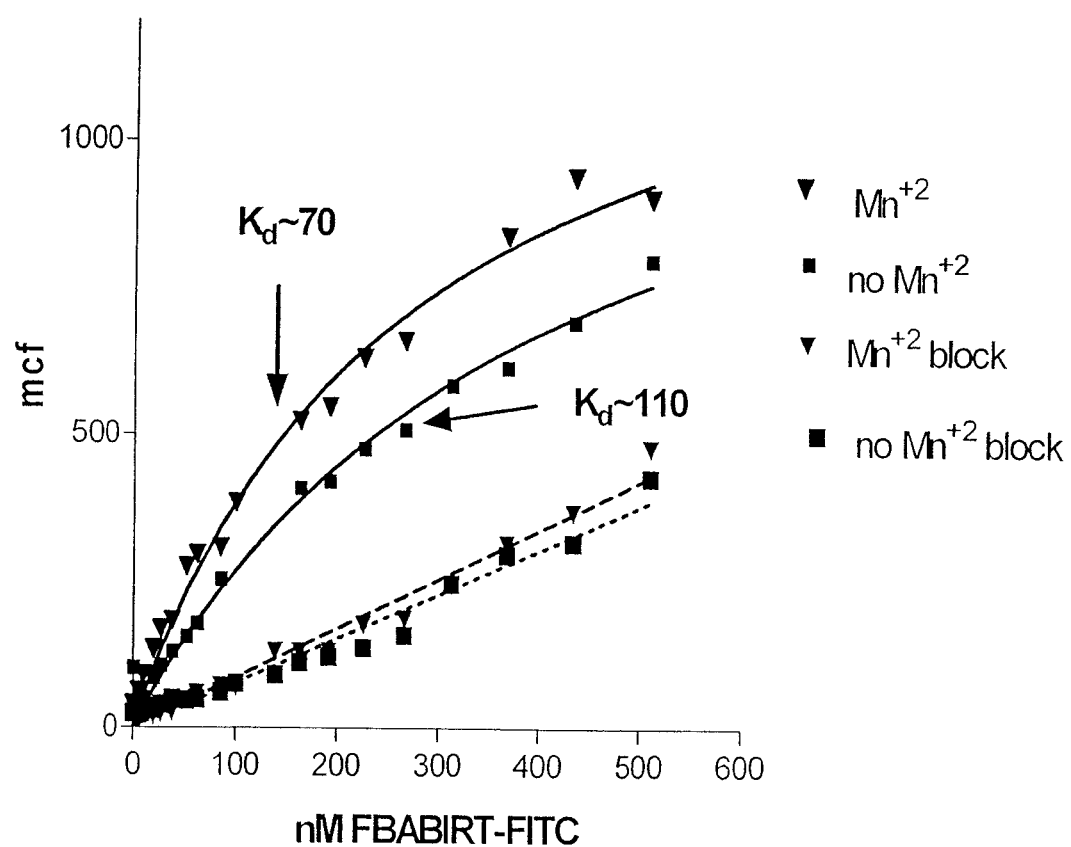
FIG. 3 shows the equilibrium binding of FBABIRT (Fluorescein labeled alkylaminO-NorBirt) to HL60 cells in the presence and absence of Mn2+.

Drug Synthesis:

The small molecule compound has been synthesized. DOTA was attached at the Chemistry Department at New Mexico State University. Standard analytical methods (including Mass Spec) showed that the DOTA linker was successfully attached to the alkylamino-NorBirt compound. The DOTA-alkylamino-NorBirt was successfully labeled with $^{213}$Bi (t1/2=45.5 minutes) in our laboratory. The radiolabeled product is shown below as a chemical structure (see FIG. 1) and on the Bioscan® (FIG. 2). If binding is unsuccessful using Lu-177 as the radioisotope and DOTA as the linker, other linkers exist and is evaluated for use if needed.

LITERATURE CITED

1. Inghirami G, Wieczorek R, Zhu B. Y, et. al. Differential Expression of LFA-1 Molecules in Non-Hodgkin's Lymphoma and Lyphoid Leukemia. *Blood.* 1988; 72:1431-1434.

2. Horst E, Radaszkiewicz T, Pals S T, et. al. Expression of the leucocyte integrin LFA-1 (CD11a/CD18) and its ligand ICAM-1 (CD54) in lymphoid malignancies are related to lineage derivation and stage of differentiation but not to tumor grade. *Leukemia.* 1991 5(10):848-53.
3. Bechter O E, Eisterer W, Thaler J, et. al. Expression of LFA-1 identifies different prognostic subgroups in patients with advanced follicle center lymphoma (FCL). *Leukemia Research.* 1999; 23(5):483-8.
4. Larson R. S, Davis T, Bolgna C, et. al. Dissociation of I Domain and global conformational changes in LFA-1: Refinement of small molecule-I domain structure-activity relationships. *Biochemistry* in press.
5. Woska J. R, Shih D, Taqueti V. R, Hogg N, Kelly T. A and Kishimoto K T. A small-molecule antagonist of LFA-1 blocks a conformational change important for LFA-1 function. *Journal of Leukocyte Biology.* 2001; 70:329-334.
6. Gursoy R. N and Siahaan T. J. Binding and internalization of an ICAM-1 peptide by the surface receptors of T-cells. *Journal of Peptide Research.* 1999; 53:414-421.
7. Hogg Nancy and Randi A. M. I Domain of β$_2$ Integrin Lymphocyte Function-associated Antigen-1 Contains a Binding Site for Ligand Intercellular Adhesion Molecule-1. *The Journal of Biological Chemistry.* 1994; 269(17): 12395-12398.
8. Kuriyama Y, Nakano M, Kawanishi Y and Toyama K. Cytofluorometric analysis of tumor cell size and follicle formation of B-cell lymphomas. *Rinsho Ketsueki.* 1995 36(4):279-285.
9. Petruzzelli L, Maduzia L and Springer T. A. Differential Requirements for LFA-1 Binding to ICAM-1 and LFA-1-Mediated Cell Aggregation. *The Journal of Immunology.* 1998; 160:4208-4216.
10. Buckley C. D, Ferguson E. D, Littler A. J, Bossy D and Simmons D L. Role of Ligands in the activation of LFA-1. *European Journal of Immunology.* 1997; 27:957-962.
11. Lub M, Kooyk Y and Figdor G. C. Ins and outs of LFA-1. *Immunology Today.* 1995; 16(10):479-483.
12. Kelly T. A, Jeanfavre, Mcneil W. D, Woska R. J and et. al. Cutting edge: A small molecule antagonist of LFA-1 mediated cell adhesion. *The Journal of Immunology.* 1999:5173-5177.
13. Last-Barney K, Davidson W, Cardozo M, Frye L L, Grygon C A, Hopkins J L, Jeanfavre D D, Pay S, Qian C, Stevenson J M, Tong L, Zindell R, Kelly T A. Binding site elucidation of hydantoin-based antagonists of LFA-1 using multidisciplinary technologies: evidence for the allosteric inhibition of a protein--protein interaction. *J Am Chem Soc.* 2001; 123(24):5643-5650.
14. Rocha M, Kruger A, Schirrmacher, et. al. Dynamic Expression Changes In Vivo of Adhesion and Costimulatory Molecules Determine Load and Pattern of Lymphoma Liver Metastasis. *Clinical Cancer Research.* 1996; 2:811-820.
15. Kang J H, Chung J K, Lee Y J, Shin J H, Jeong J M, Lee D S, Lee M C. Establishment of a human hepatocellular carcinoma cell line highly expressing sodium iodide symporter for radionuclide gene therapy. J Nucl Med. 2004; 45(9):1571-1576.
16. Norenberg J P, Krenning B J, Konings I R, De Jong M, Garmestani K, Brechbeil M W, Atcher R W, Kusewitt D F, Garmestani K, Brechbiel M W, Kvols L K. Safety and efficacy of 213Bi-[DOTA⁰, Tyr³]octreotide (Bi-DOTATOC) in peptide receptor radionuclide therapy (PRRT) of neuroendocrine tumors in a pre-clinical model. *Clinical Cancer Research*; November 2001; v7(11), suppl. S, p. 37325.
17. Delcambre C, Reman O, Henry-Amar M, Peny A M, Macro M, Cheze S, et al. Clinical relevance of gallium-67 scintigraphy in lymphoma before and after therapy. Eur J Nucl Med 2000; 27(2):176-184.
18. Johnston G S, Go M F, Benua R S, Larson S M, Andrews G A, Hubner K F. Gallium-67 citrate imaging in Hodgkin's disease: final report of cooperative group. J Nucl Med 1977; 18(7):692-698.
19. Andrews G A, Hubner K F, Greenlaw R H. Ga-67 citrate imaging in malignant lymphoma: final report of cooperative group. 1978; 19(9):1013-1019.
20. Hussain R, Christie D R, Gebski V, Barton M B, Gruenewald S M. The role of the gallium scans in primary extranodal lymphoma. J Nucl Med 1998; 39(1):95-98.
21. Gallamini A, Biggi A, Fruterro A, Pugno F, Cavallero G, Pregno P, et al. Revisiting the prognostic role of gallium scintigraphy in low-grade non-Hodgkin's lymphoma. Eur J Nucl Med 1997; 24(12):1499-1506.
22. Ben-Haim S, Bar-Shalom R, Israel O, Haim N, Epelbaum R, Ben-Shachar M, et al. Utility of gallium-67 scintigraphy in low-grade non-Hodgkin's lymphoma. J Clin Oncol 1996; 14(6):1936-1942.
23. Kumar R, Maillard I, Schuster S J, Alavi A. Utility of fluorodeoxyglucose-PET imaging in management of patients with Hodgkin's and non-Hodgkin's lymphomas. Radiol Clin N Am 2004; 42:1083-1100.
24. Macapinlac H A. The utility of 2-deoxy-2-[$^{18}$F]fluoro-d-glucose-positron emission tomography and combined positron emission tomography and computed tomography in lymphoma and melanoma. Molecular Imaging and Biology 2004; 6(4):200-2007.

The invention claimed is:

1. A method of diagnosing the existence and/or extent of a disease state or condition in tissue of a patient in which levels of LFA-1 or ICAM receptors are suspected of being or known to be elevated comprising administering to said patient an effective amount of at least one compound according to the following chemical structure:

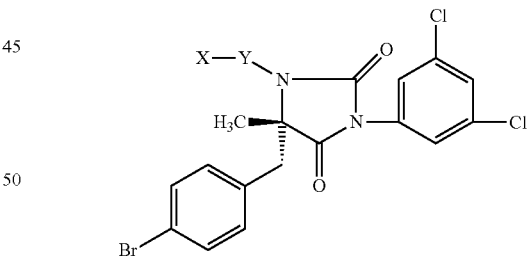

Where Y is a —(CH$_2$)$_n$Z— group where n is 4, Z is a NR group and R is H, and which group links the nitrogen of said NR group to a 1,4,7,10-tetraazacyclododecane-1,4,7,10-tetraacetic acid (DOTA) group as X and wherein said DOTA group incorporates or complexes with at least one radioisotope selected from the group consisting of $^{90}$Y, $^{111}$In, $^{177}$Lu, $^{225}$Ac, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, or a pharmaceutically acceptable salt thereof, measuring the amount of said compound which binds to said tissue in said patient, and comparing said measurement from said measuring step with a standard, wherein an elevated measurement in comparison to said standard is indicative of the existence and/or extent of said disease state or condition in said patient and said disease state or condition is an ischemia-reperfusion injury, reperfusion injury of tissue due to cardiopulmonary bypass, myocardial infarction, acute glomerulonephritis, vasculitis, reactive arthritis, dermatosis, stroke, thermal injury, hemodialysis, necrotizing enterocolitis, arthritis, rheumatoid arthritis, osteoarthritis, adult respiratory distress syndrome, shock, oxygen toxicity, septic shock, multiple organ injury syndrome secondary to trauma, Raynaud's syndrome, autoimmune thyroiditis, dermatitis, multiple sclerosis, insulin-dependent diabetes mellitus, diabetes retinopathy, uveitis, inflammatory bowel disease, Crohn's disease, systemic lupus erythematosus, psoriasis or hyperkerotosis.

2. The method according to claim 1 wherein said radioisotope is $^{90}Y$, $^{111}In$, $^{177}Lu$, or $^{213}Bi$ or a mixture thereof.

3. The method according to claim 1 wherein said DOTA group incorporates or complexes with a radioisotope selected from the group consisting of $^{90}Y$, $^{111}In$, $^{177}Lu$, $^{67}Ga$, $^{68}Ga$, and $^{213}Bi$ or a pharmaceutically acceptable salt thereof.

4. The method according to claim 3 wherein said radioisotope is $^{90}Y$, $^{213}Bi$, $^{177}Lu$ or $^{111}In$.

5. The method according to claim 3 wherein said radioisotope is $^{213}Bi$, $^{177}Lu$ or $^{111}In$.

6. The method according to claim 3 wherein said radioisotope is $^{213}Bi$, $^{90}Y$, or $^{177}Lu$.

7. The method according to claim 3 wherein said radioisotope is $^{213}Bi$.

8. The method according to claim 1 wherein said compound is

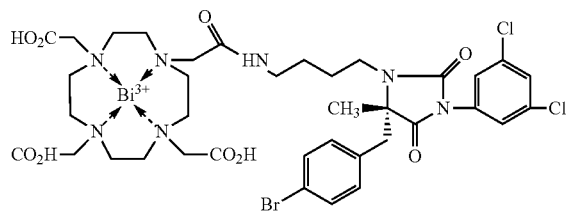

or a pharmaceutically acceptable salt thereof.

9. The method according to claim 1 wherein said disease state or condition is ischemia-reperfusion injury, reperfusion injury of tissue due to cardiopulmonary bypass, myocardial infarction, acute glomerulonephritis, vasculitis, reactive arthritis, ulcerative colitis or necrotizing enterocolitis.

10. The method according to claim 1 wherein said disease state or condition is reactive arthritis, arthritis, rheumatoid arthritis, osteoarthritis, inflammatory bowel disease, Crohn's disease, systemic lupus erythematosus, ulcerative colitis; or necrotizing enterocolitis.

11. The method according to claim 1 wherein said disease state or condition is ischemia-reperfusion injury, reperfusion injury of tissue due to cardiopulmonary bypass, myocardial infarction, acute glomerulonephritis, vaculitis, reactive arthritis, ulcerative colitis or necrotizing enterocolitis.

12. The method according to claim 1 wherein said disease state or condition is arthritis, rheumatoid arthritis, osteoarthritis or reactive arthritis.

13. The method according to claim 1 wherein said disease state or condition is inflammatory bowel disease, Crohn's disease, ischemia-reperfusion injury, myocardial infarction or acute glomerulonephritis.

14. The method according to claim 1 wherein said autoimmune disease is inflammamtory bowel disease, Crohn's disease, ulcerative colitis or necrotizing enterocolitis.

15. A method of treating an ICAM-1/LFA-1 mediated disease state or condition in a patient in need comprising administering to said patient an effective amount of at least one compound according to the following chemical structure:

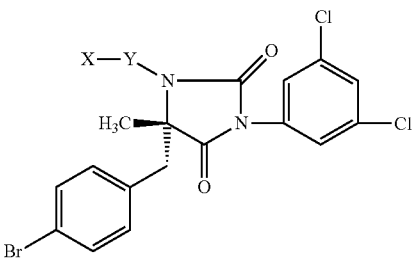

Where Y is a —$(CH_2)_nZ$— group where n is 4, Z is a NR group and R is H, and which group links the nitrogen of said NR group to a 1,4,7,10-tetraazacyclododecane-1,4,7,10-tetraacetic acid (DOTA) group as X and wherein said DOTA group incorporates or complexes with at least one radioisotope selected from the group consisting of $^{90}Y$, $^{111}In$, $^{177}Lu$, $^{225}Ac$, $^{213}Bi$, $^{67}Ga$, $^{68}Ga$, $^{64}Cu$, $^{67}Cu$, $^{71}As$, $^{72}As$, $^{76}As$, $^{77}As$, $^{65}Zn$, $^{76}Br$, $^{48}V$, $^{49}V$, $^{203}Pb$, $^{209}Pb$, $^{212}Pb$, $^{166}Ho$, $^{153}Pm$, or a pharmaceutically acceptable salt thereof, wherein said disease state or condition is an ischemia-reperfusion injury, reperfusion injury of tissue due to cardiopulmonary bypass, myocardial infarction, acute glomerulonephritis, vasculitis, reactive arthritis, dermatosis, stroke, thermal injury, hemodialysis, necrotizing enterocolitis, arthritis, rheumatoid arthritis, osteoarthritis, adult respiratory distress syndrome, shock, oxygen toxicity, septic shock, multiple organ injury syndrome secondary to trauma, Raynaud's syndrome, autoimmune thyroiditis, dermatitis, multiple sclerosis, insulin-dependent diabetes mellitus, diabetes retinopathy, uveitis, inflammatory bowel disease, Crohn's disease, systemic lupus erythematosus, psoriasis or hyperkerotosis.

16. The method according to claim 15 wherein said radioisotope is $^{90}Y$, $^{111}In$, $^{177}Lu$, or $^{213}Bi$ or a mixture thereof.

17. The method according to claim 15 wherein said DOTA group incorporates or complexes with a radioisotope selected from the group consisting of $^{90}Y$, $^{111}In$, $^{177}Lu$, $^{67}Ga$, $^{68}Ga$, and $^{213}Bi$ or a pharmaceutically acceptable salt thereof.

18. The method according to claim 15 wherein said radioisotope is $^{90}Y$, $^{213}Bi$, $^{177}Lu$ or $^{111}In$.

19. The method according to claim 15 wherein said radioisotope is $^{213}Bi$ $^{177}Lu$ or $^{111}In$.

20. The method according to claim 15 wherein said radioisotope is $^{213}Bi$, $^{90}Y$, or $^{177}Lu$.

21. The method according to claim 15 wherein said radioisotope is $^{213}Bi$.

22. The method according to claim 15 wherein said compound is

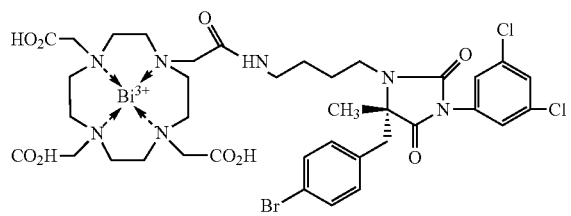

or a pharmaceutically acceptable salt thereof.

23. The method according to claim 15 wherein said disease state or condition is ischemia-reperfusion injury, reperfusion injury of tissue due to cardiopulmonary bypass, myocardial infarction, acute glomerulonephritis, vasculitis, reactive arthritis, ulcerative colitis or necrotizing enterocolitis.

24. The method according to claim 15 wherein said disease state or condition is reactive arthritis, arthritis, rheumatoid arthritis, osteoarthritis, inflammatory bowel disease, Crohn's disease, systemic lupus erythematosus, ulcerative colitis or necrotizing enterocolitis.

25. The method according to claim 15 wherein said disease state or condition is ischemia-reperfusion injury, reperfusion injury of tissue due to cardiopulmonary bypass, myocardial infarction, acute glomerulonephritis, vaculitis, reactive arthritis, ulcerative colitis or necrotizing enterocolitis.

26. The method according to claim 15 wherein said disease state or condition is arthritis, rheumatoid arthritis, osteoarthritis or reactive arthritis.

27. The method according to claim 15 wherein said disease state or condition is inflammatory bowel disease, Crohn's disease, ischemia-reperfusion injury, myocardial infarction, acute glomerulonephritis, vasculitis or reactive arthritis.

28. The method according to claim 15 wherein said autoimmune disease is inflammamtory bowel disease, Crohn's disease, ulcerative colitis; or necrotizing enterocolitis.

* * * * *